United States Patent [19]

Sabater et al.

[11] Patent Number: 4,707,223

[45] Date of Patent: Nov. 17, 1987

[54] APPARATUS FOR MEASURING THE STATE OF FORMATION OF A SHEET OF PAPER

[75] Inventors: Jacques Sabater, Gif/Yvette; Serge Bauduin, La Tronche, both of France

[73] Assignee: Centre Technique de l'Industrie des Papiers Cartons et Celluloses, France

[21] Appl. No.: 754,162

[22] Filed: Jul. 12, 1985

[30] Foreign Application Priority Data

Jul. 17, 1984 [FR] France ................. 84 11493

[51] Int. Cl.⁴ ............................ D21F 7/00; D21F 7/06
[52] U.S. Cl. ..................................... 162/262; 162/263; 356/366; 356/367
[58] Field of Search ............... 162/263, 198, 252, 258, 162/259; 356/366, 367, 364

[56] References Cited

U.S. PATENT DOCUMENTS

| | | | |
|---|---|---|---|
| 3,525,871 | 8/1970 | Lehtinen | 250/219 |
| 3,807,868 | 4/1974 | Simila | 356/118 |
| 4,266,142 | 5/1981 | Crawford | 250/572 |
| 4,555,177 | 11/1985 | Barrett | 356/367 |
| 4,586,820 | 5/1986 | Yokoyama et al. | 356/367 |

FOREIGN PATENT DOCUMENTS 1025767 6/1983 U.S.S.R. ............................ 162/252

OTHER PUBLICATIONS

Andersen; "An On-line Inspection Device", *TAPPI*, vol. 62, No. 6, Jun. 1979, p. 69.

*Primary Examiner*—Steve Alvo
*Attorney, Agent, or Firm*—Parkhurst & Oliff

[57] ABSTRACT

This invention relates to an apparatus for continuously measuring the state of formation of a sheet of paper which comprises: —means for moving a sheet of paper at a predetermined speed; —a light source directing a laser beam through said sheet; —a means for picking up the laser light transmitted, then for converting it into an electrical signal; —electronic processing means for separating this electrical signal into two components; —means for calculating from these components the index I representative of the state of formation; —a means for displaying the value of this index I; wherein the laser beam is polarized, and the apparatus further comprises, between the sheet and the means for picking up the laser light transmitted, a polarizer of which the axis of polarization is perpendicular to the axis of polarization of the laser beam transmitted.

4 Claims, 4 Drawing Figures

APPARATUS FOR MEASURING THE STATE OF FORMATION OF A SHEET OF PAPER

The present invention relates to an apparatus for continuously measuring the state of formation of a sheet of paper.

The expression "formation of a sheet of paper" designates the more or less regular distribution of the fibrous matter in the plane of the sheet. This notion is well known to the man skilled in the art and is referred to as "formation".

The formation is generally assessed visually by examining the transparency of the sheet of paper placed in front of a light box. Although wide-spread, this is a subjective method which therefore necessitates a good knowledge of the paper-making process and long practice. In addition, by definition, this method does not furnish any data or measurement, whilst the manufacture of high-quality paper requires objective tools of analysis.

Furthermore, this method can only be effected a posteriori on sheets of paper taken at the end of a roll and not during manufacture thereof.

To overcome this drawback, French Pat. No. 1 566 138 suggests a device which consists in sending onto the paper a light beam, then in converting the beam transmitted into an electrical signal, finally in measuring the ratio between the AC component and the DC component obtained. This process is difficult to carry out on a paper-making machine in which the sheet is in movement, as it does not tolerate the oscillations of this sheet. In addition, the results obtained are not always very reliable, apart from the fact that this method is limited to papers of low G.S.M. (grammes per square meter).

It has recently been suggested to replace the light beam by a laser beam issuing from a laser diode, the light transmitted through the sample then being converted into an electrical signal. A computer then determines the root mean square value (RMS) of several spectral bands and displays the result of these values. This is a complex and expensive device which does not avoid the disturbances in measurement provoked by the micro-holes in the sheet to be analysed. In fact, upon use, it has been observed that certain papers presenting such micro-holes allow the light to pass, which disturbs the calculations of RMS.

It is an object of the present invention to overcome these drawbacks. It relates to an apparatus for continuously measuring the state of formation of a sheet of paper, which is economical to manufacture, easy to carry out and which is insensitive to the microholes.

This apparatus for continuously measuring the state of formation of a sheet of paper which comprises:
  means for moving a sheet of paper at a predetermined speed;
  a light source directing a laser beam through said sheet;
  a means for picking up the laser light transmitted, then for converting it into an electrical signal;
  electronic processing means for separating this electrical signal into two components and for calculating from these components the index I representative of the state of formation;
  a means for displaying the value of this index I; is characterized in that:
  the laser beam is polarized,
and the apparatus further comprises, between the sheet and the means for picking up the laser light transmitted, a polarizer of which the axis of polarization is perpendicular to the axis of polarization of the laser beam transmitted.

In other words, the laser beam is polarized and the pick-up apparatus is likewise polarized with respect to the axis of polarization of the laser beam transmitted.

Advantageously, in practice:
  the laser is either a gas laser (He - Ne) or a junction laser associated with an optical collimation system;
  the laser beam emitted is firstly reflected by a prism or a mirror, then passes through the moving sheet, and finally is again reflected by a mirror before penetrating in the polarizer;
  the polarizer is associated with an aspherical lens which projects onto the measuring member the image of the part of the sheet to be analyzed;
  the apparatus comprises, in the vicinity of the sheet of paper to be analyzed, passages, conical for example, presenting a lateral admission of compressed air;
  the means for converting the laser light into an electrical signal is a transducer, and the electrical signal emitted and amplified is separated into two components, namely a high frequency component A, and a low frequency component B, by passage in an assembly comprising a low-pass filter and a high-pass filter;
  the electrical signal is separated into two components: high-frequency A and low-frequency B, by passage in a low-pass filter, following which the high frequency component A is deduced by subtraction of the component B from the input signal;
  the means for calculating index I comprises: . a means for calculating the RMS value of the high-frequency component A by an analog module, . a means for determining the mean value M of the low-frequency component B by a low-pass filter, . a means for effecting the ratio:

$$I = \frac{\text{RMS value at instant } (t)}{\text{mean value } M \text{ at same instant } (t)}$$

The invention will be more readily understood on reading the following description with reference to the accompanying drawings, in which.

Figure 1:
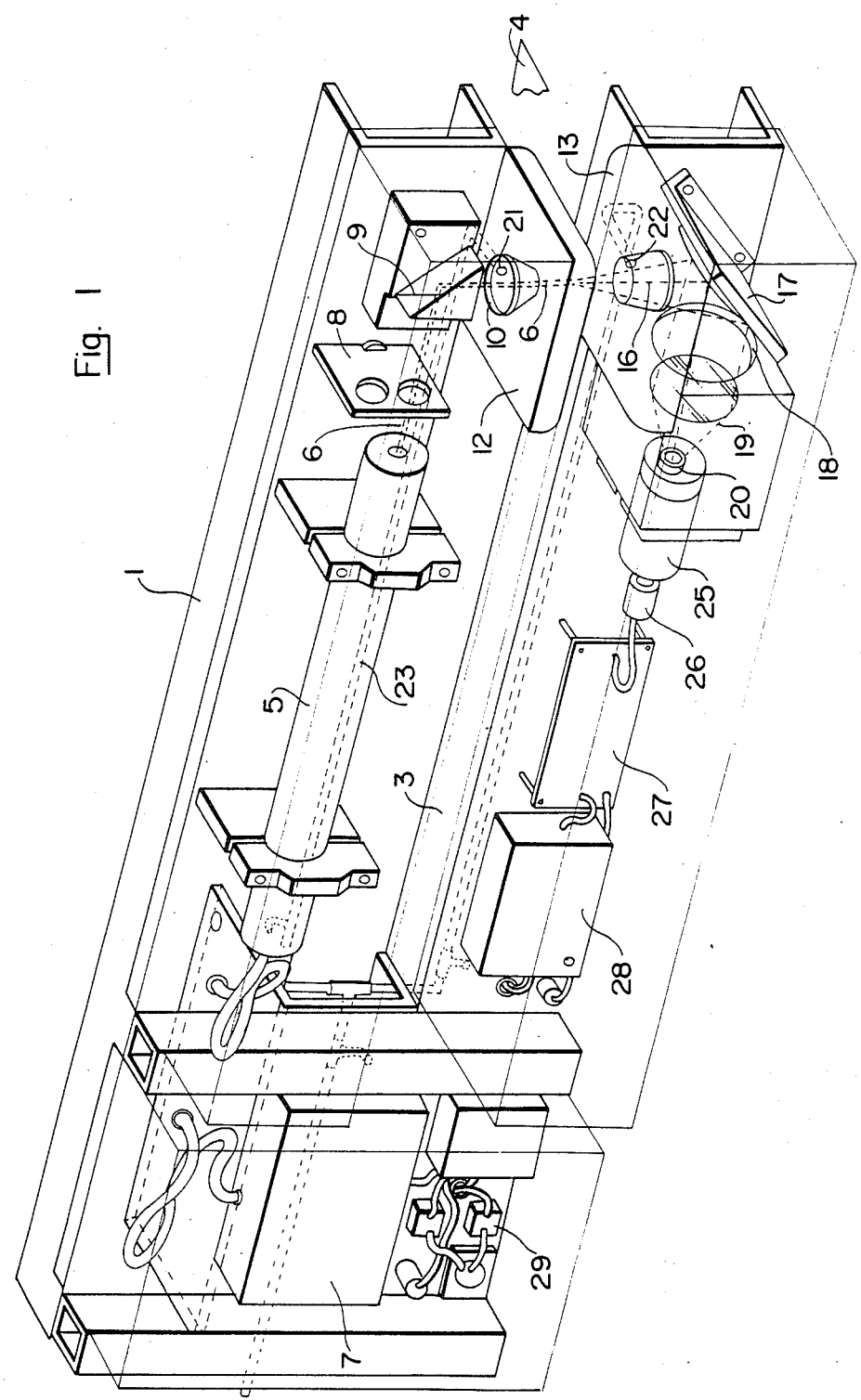
FIG. 1 is a general perspective view of an apparatus for measuring the formation of a sheet in accordance with the invention.
Figure 2:
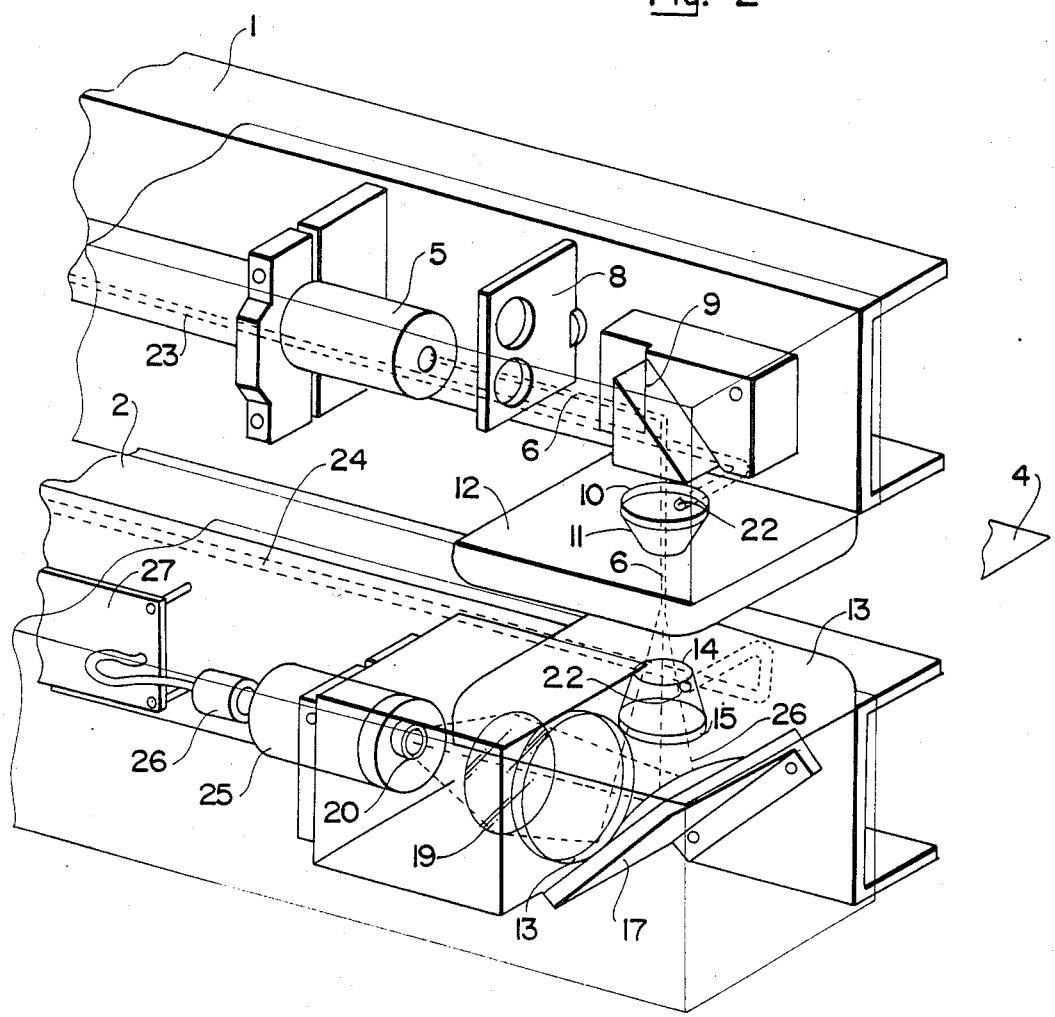
FIG. 2 is an enlarged view of the measuring head of the invention.

Referring now to the drawings, the apparatus according to the invention illustrated in FIGS. 1 and 2 comprises a U-shaped chassis 1, 2, 3 between the branches of which the sheet of paper, symbolized by reference 4, passes. This sheet is moved by conventional means (not shown) forming an integral part of a paper-making machine.

The upper horizontal branch 1 of the apparatus comprises a He-Ne gas laser 5, for example of two mW, emitting a polarized beam 6. This laser 5 is supplied in known manner by means of a cable connected to a conventional laser supply 7.

On the path of the polarized laser beam 6 there is possibly interposed a rotary lens device 8, divergent or convergent, adapted to modify the dimension of the laser spot 6 on the moving sheet 4.

The beam 6 emitted is then reflected by a prism 9 with total reflexion, to penetrate in a blade 10 with parallel faces forming a window. This blade 10 is placed at the large base of a cone 11, the apex of wich is directed downwardly in the direction of the sheet 4. This solid cone 11 is cut in a horizontal plate 12.

Symmetrically, a second plate 13 also comprises a solid cone 14 aligned with 11 which is associated with a second blade 15 with parallel faces forming a window.

The transmitted beam 16 which emerges from this blade 15 then arrives on a plane mirror 17 inclined at 45°.

The transmitted and reflected beam then passes through a polarizer 18, the axis of polarization of which is perpendicular to the axis of polarization of the transmitted laser beam 16 so as to eliminate the direct light during the presence of micro-holes or voids in the sheet 4 to be analyzed.

The polarizer 18 is associated by its rear face with a focalizing aspherical lens 19 which concentrates on the photoelectric measuring cell 20 the image of the illuminated part of the sheet 4 to be analyzed.

In order to prevent deposits of dirt or dust in the solid cones 11 and 14, these cones comprise admissions 21, 22 supplied with compressed air via conduits 23, 24.

The silicon photoelectric cell 20, forming transducer (photodiode), is mounted at the end of a cylindrical support unit 25. This cell converts the light treated into an electrical signal.

This electrical signal emerging from cell 20 is received by a tap 26 which transmits it to the electronic pre-ampli board 27 associated with its supply 28.

The apparatus also comprises, in known manner, control relays referenced 29.

Figure 3:
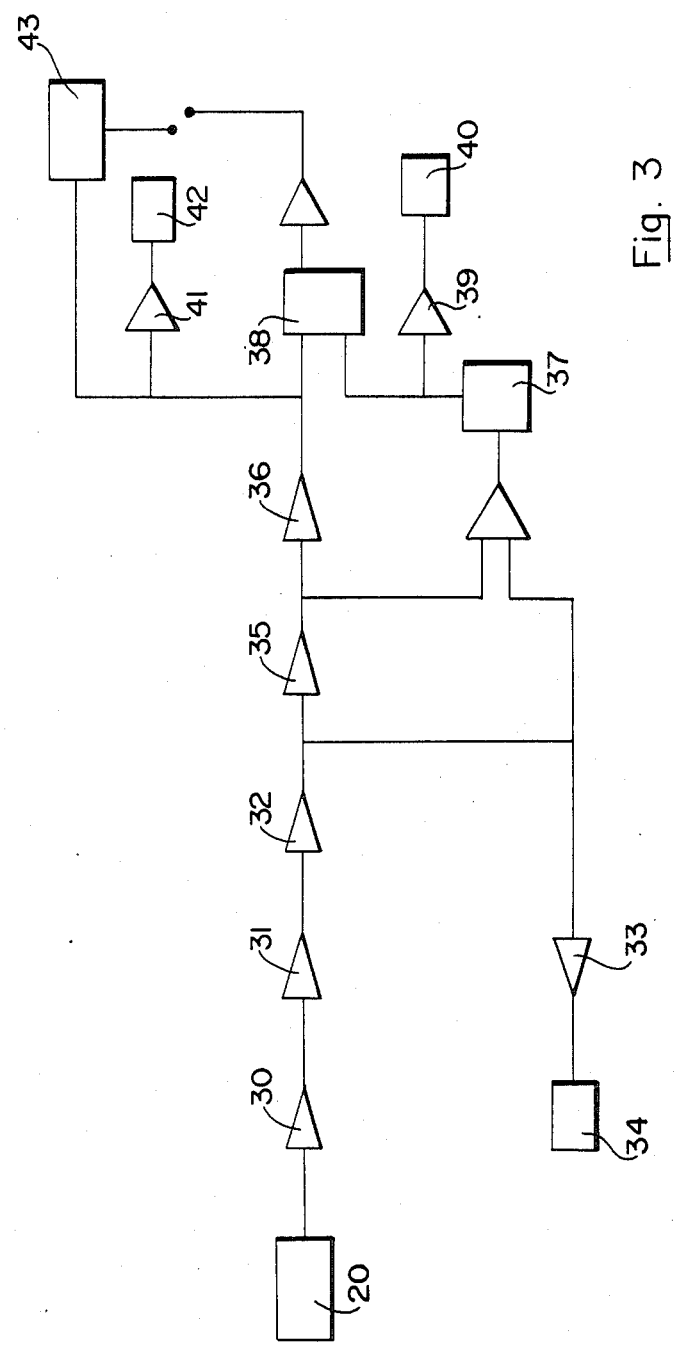
FIG. 3 is a symbolic representation of the electronic signal processing part.

The device for analyzing the electrical signal essentially consists (cf. FIGS. 3 and 4), by an appropriate electronic filtering, in separating this signal into two components: a so-called high-frequency component A and low-frequency component B.

The high-frequency component A, called "formation", which therefore corresponds to the high-frequency part of the spectrum of the signal, i.e. to the variations existing on sheet 4 with wave lengths less than a predetermined maximum, is characterized by its root mean square (RMS) value or effective value.

The low-frequency component B, called by analogy "gsm", corresponds to the low-frequency part of the spectrum of the signal, and even to its frequency 0, i.e. to the phenomena which are reproduced on the sheet 4 with wave lengths greater than a predetermined minimum. This component B is approximately a reverse function of the gsm and is characterized by its mean value M.

The index I of formation of the sheet furnished by the apparatus is the ratio between this RMS value of the high-frequency component A and the mean value M of the low-frequency gsm component B.

The silicon photocell 20 mounted as a photovoltaic cell (cf. FIG. 3) is followed by a current-voltage converter 30. An amplifier 31 allows long-distance links between the measuring cabinet and head.

The pass band of the electrical signal emitted is about one hundred kHz at −3 dB.

The electrical signal coming from the amplifier 31 penetrates on another variable gain amplifier 32 by switching. This particular assembly makes it possible to conserve, whatever the gain, a constant low negative feedback value, minimizing the zero adjustments (offset adjustment).

An amplifier-comparator 33 enables saturation of the amplifier 32 to be displayed on a LED 34.

The high-pass filtering necessary before calculating the RMS value is obtained by subtracting from the signal emitted by 32 the low-frequency part obtained at the output of the amplifier 35, which is a low-pass filter with cut-off frequency $f_1$.

This cut-off frequency $f_1$ is adapted to the predetermined speed of displacement of the sheet 4, so that the ratio between this speed and the cut-off frequency $f_1$ is close to twenty centimeters.

On the other hand, the mean value M of the signal is obtained by a low-pass filter 36 of variable cut-off frequency $f_2$. The ratio between the speed V of the sheet 4 analyzed and this cut-off frequency $f_2$ is close to two meters.

The RMS value is obtained with the aid of the analog computing module 37 comprising an integrated low-pass filter having a cut-off frequency $f_3$ identical to $f_2$, so that the results of the division are coherent. The values $f_1$, $f_2$ and $f_3$ are switched together.

The division of the output of the RMS value at the output of the amplifier 36 is effected by a divider module 38.

A comparator 39 detects and indicates with the aid of a LED 40 a saturation of the RMS module 37.

An amplifier-comparator 41 detects and indicates with the aid of a LED 42 a voltage lower than one hundred millivolts at the output of 36.

A digital voltmeter 43 forms display of the apparatus. This voltmeter 43 is supplied through a dividing-by-ten bridge, by the output signal given to the amplifier. The outside adjustment of zero is effected on amplifier 32 and is effected with laser 5 extinguished.

Thus, the output ratio $$\frac{10 \times RMS}{M}$$

of the divider module 38 is displayed in volts.

Figure 4:
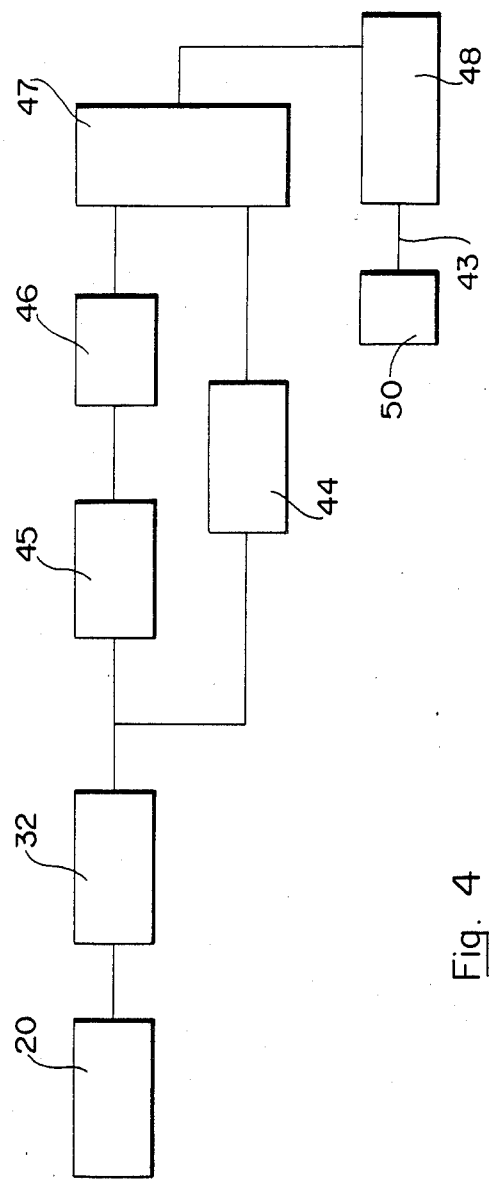
FIG. 4 is a likewise symbolic representation of a variant embodiment of this electronic measuring part.

In the simplified embodiment shown in FIG. 4, the signal issuing from amplifier 32 is separated into two components, one directed onto a low-pass filter 44, the other onto a high-pass filter 45, itself associated with an analog RMS module 46. The low-pass filter and the analog RMS module 46 are connected to an analog divider module 47 which, by an optional low-pass filter 48, emits an output signal 49 representative of value I. This value I is displayed at 50 in known manner, either on a digital display or on a recording display.

The apparatus according to the invention presents numerous advantages over those proposed heretofore. For example:

the fact that this apparatus is easy to construct and to use;

the principle of calculation of index I which is simple;

the measurement I of the formation effected is independent of the gsm of the paper treated since the existence of the quotient makes it possible to be freed from the fact that the same quality of formation gives more modulations to the signal on a paper of low gsm than on a thick paper;

thanks to the use of a polarized laser which emits a thin beam, the apparatus is virtually insensitive to oscillations of the sheet up to amplitudes of the order of a centimeter;

thanks to the considerable light intensity of the polarized laser, the apparatus may be used on papers of high gsm, even beyond 250 g/m²;

the use of polarized light which makes it possible to attenuate considerably the influence of the micro-holes or voids existing in the sheet 4 to be analyzed and considerably influencing the value of the formation.

This apparatus may consequently be successfully used on the very machines for manufacturing the paper, even on existing machines, which could not be done in practice heretofore.

What is claimed is:

1. An apparatus for determining a state of formation of paper linearly moving in a plane, comprising:

light source means, located on a first side of said plane, for transmitting a laser beam through said plane, said laser beam being polarized in a first direction;

polarizing means for polarizing said laser beam after said laser beam is transmitted through said plane, said polarizing means being located wherein the direction of polarization of said polarizing means is substantially perpendicular to said first direction, and wherein light passing through said plane due to voids in said moving paper is eliminated;

light sensing means for receiving said laser beam after said laser beam passes through said polarizing means, and for converting said laser beam into an electrical signal;

means for separating said electrical signal into a high frequency component and a low frequency component;

means for calculating a RMS value of said high frequency component;

means for calculating a mean value of said low frequency component; and means for dividing said RMS value by said mean value to determine a state of formation of paper.

2. An apparatus according to claim 1 wherein said separating means further comprises means for producing said high frequency component by subtracting said low frequency component from said electrical signal.

3. An apparatus according to claim 1 wherein said separating means comprises low-pass filter means for producing said low frequency component from said electrical signal, and high-pass filter means for producing said high frequency component from said electrical signal.

4. An apparatus according to claim 1 further comprising an aspherical lens located between said polarizing means and said light sensing means, for focussing said laser beam onto said light sensing means.

* * * * *